United States Patent [19]

Lay

[11] 4,067,326

[45] Jan. 10, 1978

[54] POSTURE SUPPORTING APPARATUS

[76] Inventor: Kenneth George Lay, 33 Goose Pond Road, Lincoln, Mass. 01773

[21] Appl. No.: 716,125

[22] Filed: Aug. 20, 1976

[51] Int. Cl.[2] .......... A61F 5/00

[52] U.S. Cl. .......... 128/69

[58] Field of Search .......... 128/69, 70, 71, 72, 128/82, 83

[56] References Cited

U.S. PATENT DOCUMENTS

| | | | |
|---|---|---|---|
| 1,099,092 | 6/1914 | Hyatt | 128/70 |
| 2,904,039 | 9/1959 | Weissenberg | 128/69 |
| 3,042,025 | 7/1962 | Jackson | 128/70 X |
| 3,866,605 | 2/1975 | Stakeman | 128/70 |

FOREIGN PATENT DOCUMENTS

| | | | |
|---|---|---|---|
| 1,805,414 | 5/1970 | Germany | 128/70 |

*Primary Examiner*—John D. Yasko

*Attorney, Agent, or Firm*—Jerry Cohen

[57] ABSTRACT

Posture correcting apparatus comprises a straight pipe to be used at angles of less than 90° to horizontal for engaging the spinal area of a user over a width of 3 to 6 inches and a length of about 2-3 feet, substantially fully along the spine, to allow gravity to gently exercise the back muscles of the user.

8 Claims, 4 Drawing Figures

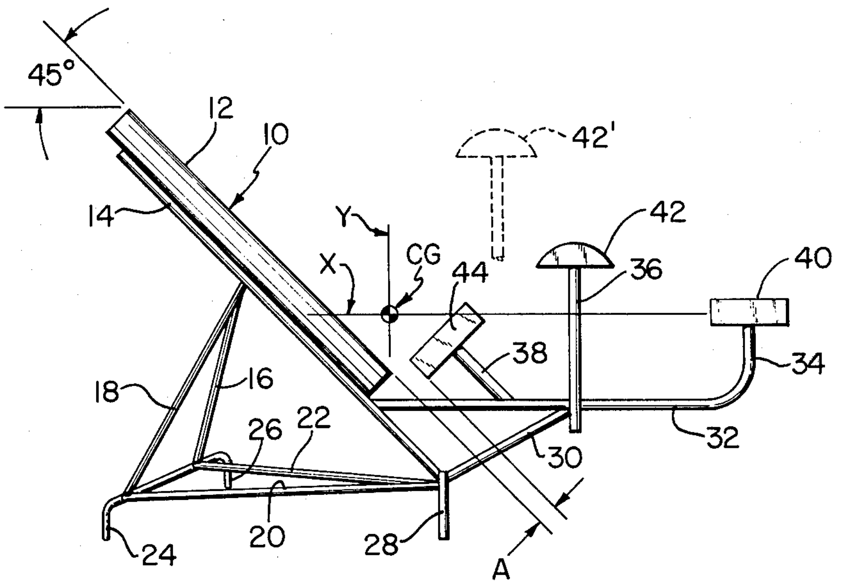
FIG. 1
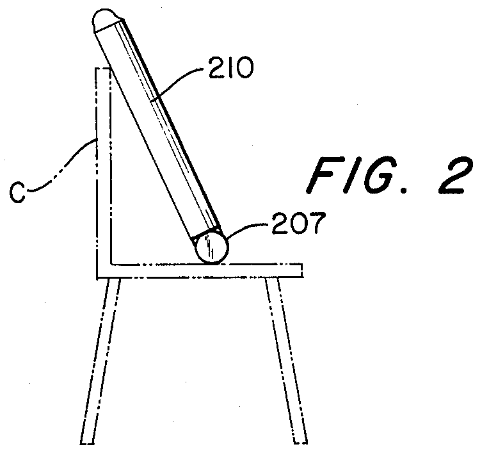
FIG. 2
FIG. 4
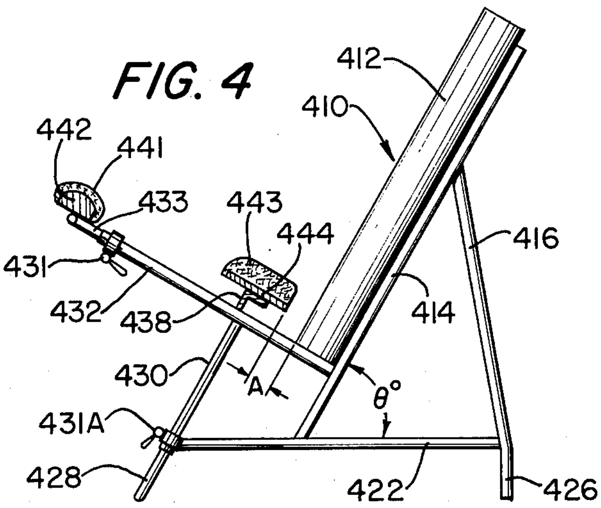
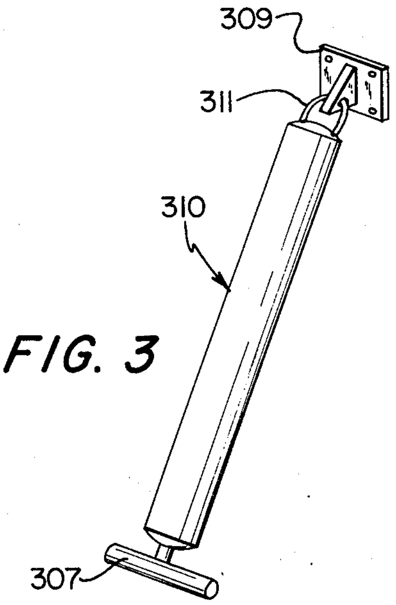
FIG. 3

POSTURE SUPPORTING APPARATUS

BACKGROUND OF THE INVENTION

The present invention relates primarily to posture correcting and is particularly characterized in providing an economical, effective apparatus for that purpose and for rest.

Posture correcting apparatus is exemplified by the following U.S. patents:

| Patent No. | Date | Inventor(s) |
|---|---|---|
| 3,759,252 | 9/18/73 | Berman |
| 3,878,840 | 4/22/75 | Esbelin |
| 3,320,949 | 5/23/67 | Hatfield |
| 3,866,605 | 2/18/75 | Stakeman |
| 3,081,085 | 3/12/63 | De Girolamo |

It is an important object of the present invention to provide effective strengthening of back muscles usable in establishing correct posture.

It is a further object of the invention to provide simple, economic apparatus for the preceding purpose.

It is a further object of the invention to provide multiple uses consistent with one or more of the preceding objects, including provision of muscular stimulation to other portions of the body to which the device is applied.

It is a further object of the invention to accomplish one or more of the foregoing objects consistent with apparatus which lends itself to interior decorator styling.

SUMMARY OF THE INVENTION

In accordance with the invention, a pipe element is arranged at 30°–70° to horizontal in a self supported chair apparatus, or usable in an existing chair, or arrangeable between a floor and ceiling using them for support. The pipe form element is straight and has a diameter of 3–6 inches, preferably around two inches, to engage the spine and allow the upper back muscles to be gently exercised by the downward gravity pull. A seat may be provided, spaced 2 inches from the straight pipe or more generally 2–4 inches perpendicularly to and spaced therefrom. The center of gravity of the user itself is established 1–3 inches from each of the seat and the straight pipe element and this center of gravity may essentially but not necessarily coincide with the center of gravity of the apparatus. Additionally, an adjustable rest carried on the apparatus may be provided for knee and foot support or alternatively, separate knee and foot rest elements may be provided.

Other objects, features and advantages of the invention will be apparent from the following detailed description of preferred embodiments taken in connection with the accompanying drawing, in which:

BRIEF DESCRIPTION OF THE DRAWING

FIG. 1 is an isometric view of a first embodiment of the invention;

FIG. 2 is a side view of a second embodiment of the invention;

FIG. 3 is an isometric view of a third embodiment of the invention; and

FIG. 4 is a side view of a fourth embodiment of the invention.

DETAILED DESCRIPTION OF PREFERRED EMBODIMENTS

It will be understood that features may be transposed from one embodiment to the other in permatations additional to those shown.

FIG. 1 shows an apparatus 10 in accordance with the present invention comprising a straight pipe element of at least 30 inches in length, covered with upholstery and supported on a backing element 14 which in turn is supported from a truss work comprising legs 16, 18, 20 and 22 and these are in turn supported on legs 24, 26 and 28. An additional arm 30 supports a bar 32 which via bar 34, 36 and 38 carries a foot rest 40, a knee support 42 and a seat 44. X and Y coordinates of the center of gravity of the user, coinciding at the center of gravity, CG, are indicated. The user who sits on seat 44 would have his back and head rest against the upholstered pipe 12. A phantom position of the knee rest 42 is shown at 42' with the original 42 serving as a foot rest, thereby allowing the knees to be placed high when the apparatus changed when indicated by 42'. The bar 14 makes an angle of 45 degrees with respect to the horizontal surface on which the apparatus rests. The center of gravity CG is over the geometric envelope defined by the supporting truss work, 20, 22 and 18.

A second embodiment is shown wherein a pipe 210 with upholstered covering sits on a conventional chair C seat to provide the necessary support. This embodiment has cross pipe 207 at its base to prevent the support from rolling from side to side.

FIG. 3 shows a pipe supported by a swivel 311 from a wall plate 309 and having a crossing pipe 307 at its foot resting on the floor. Either of the devices 309/311 or 307 can be used to avoid twisting of the pipe 310 in use.

FIG. 4 shows embodiment 410 in which the pipe 412 has a 3–6 inch diameter, preferably 4 inches, cushioned support and an arm extension 422 via locking collar 431 which is adjustable to stretch out the foot and knee support and provides a seat cushion at 443/444. A support is provided as shown at 422–430 or it may be as in any of the preceding embodiments. The user may reverse the use of the apparatus by placing his shoulders or head on 442 resting his buttocks on 443 and running his legs up the other way along 412 for an additional exercise supplementing the basic exercise of sitting on the seat 443/444 with his feet on the support 412 and the back essentially supported over its full length and in a 4 inch width with the muscles being urged downward by gravity. The additional exercise strengthens the back of the legs. An extension 428 of the let 430 may be extended after loosening lock 431A to adjust the angle $\theta$ of 412/414 with respect to horizontal to meet different exercise needs.

It is evident that those skilled in the art, once given the benefit of the foregoing disclosure, may now make numerous other uses and modifications of, and departures from the specific embodiments described herein without departing from the inventive concepts. For instance, muscle stimulation can be provided in other parts of the body by working gravity against supporting the muscle area on the apparatus. Consequently, the invention is to be construed as embracing each and every novel feature and novel combination of features present in, or possessed by, the apparatus and techniques herein disclosed and limited solely by the scope and spirit of the appended claims.

What is claimed is:

1. Posture correcting and muscle stimulating apparatus comprising means defining a straight pipe form element extending at an acute angle to horizontal for engaging the spinal area of a user over a width of 3–6 inches and a length of at least 2 feet, means for supporting the pipe form element at said angle and in a height relation to allow the user to rest with his spine essentially fully engaging the pipe form element and adjacent muscle areas of at least the upper back free of such engagement allowing gravity to gently exercise at least the upper back muscles of the user.

2. Apparatus in accordance with claim 1 and further comprising a seat arranged perpendicular to and spaced from the said spine engaging element.

3. Apparatus in accordance with claim 2 and further comprising additional adjustable means for providing foot support for the user.

4. Apparatus in accordance with claim 3 and further comprising means for adjusting seat to foot distance.

5. Apparatus in accordance with claim 2 wherein the center of gravity of the user is established between the seat and the support by the arrangement of the apparatus.

6. Apparatus in accordance with claim 1 and further comprising means for adjusting the angle of spinal support with respect to horizontal.

7. Apparatus in accordance with claim 2 and further-comprising means for supporting a user under the knees and at the feet.

8. Apparatus in accordance with claim 1 wherein said angle is 30°–70°.

* * * * *